United States Patent [19]
West

[11] Patent Number: 5,731,582
[45] Date of Patent: Mar. 24, 1998

[54] SURFACE SENSOR DEVICE

[75] Inventor: Ian Philip West, Cardiff, United Kingdom

[73] Assignee: Johnson & Johnson Medical, Inc., Arlington, Tex.

[21] Appl. No.: 681,592

[22] Filed: Jul. 29, 1996

[30] Foreign Application Priority Data

Jul. 31, 1995 [GB] United Kingdom ............... 9515649

[51] Int. Cl.⁶ .................................................. G01J 5/08
[52] U.S. Cl. ............................... 250/341.8; 250/341.2
[58] Field of Search ........................ 250/341.1, 341.8, 250/341.2

[56] References Cited

U.S. PATENT DOCUMENTS 5,139,339  8/1992  Courtney et al. ............... 250/341.8

FOREIGN PATENT DOCUMENTS

| A 479322 | 4/1992 | European Pat. Off. . |
| 2 127 068 | 10/1972 | France . |
| 3204258 | 8/1983 | Germany ............... 250/341.8 |
| 2061496 | 5/1981 | United Kingdom . |

*Primary Examiner*—Edward J. Glick

[57] ABSTRACT

A surface sensor device (1) with an electromagnetic radiation emitter (3) and a radiation detector (2) disposed on opposite sides of an instrument outlet (6), which instrument outlet (6) is required to be placed in close proximity to a surface (30). The surface sensor (1) also having a member (8) disposed in the path of the emitted radiation and the radiation reflected from the surface (30). The member (8) allows a portion of the emitted radiation to pass within it from the emitter (3) to the detector (2) while providing a path for a further portion of the radiation to pass through the member (8) towards the surface (30) for scattering and reflection by which means light is returned to the member (8) back towards the detector (2).

9 Claims, 4 Drawing Sheets

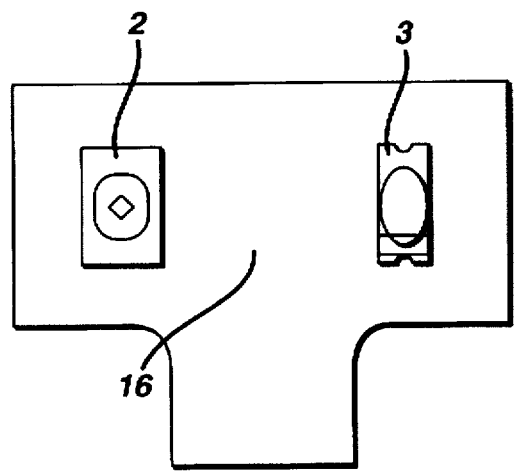
FIG. 6
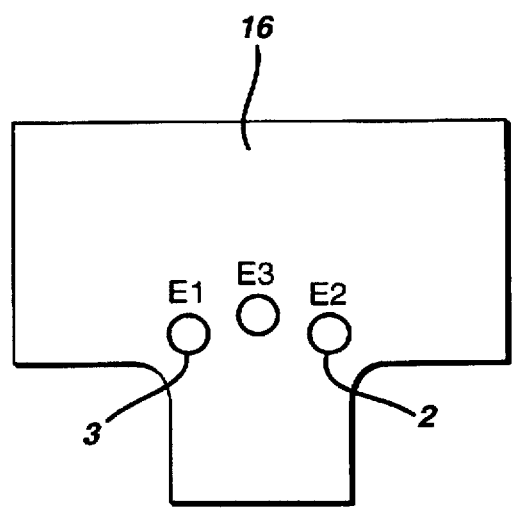
FIG. 7
FIG. 8
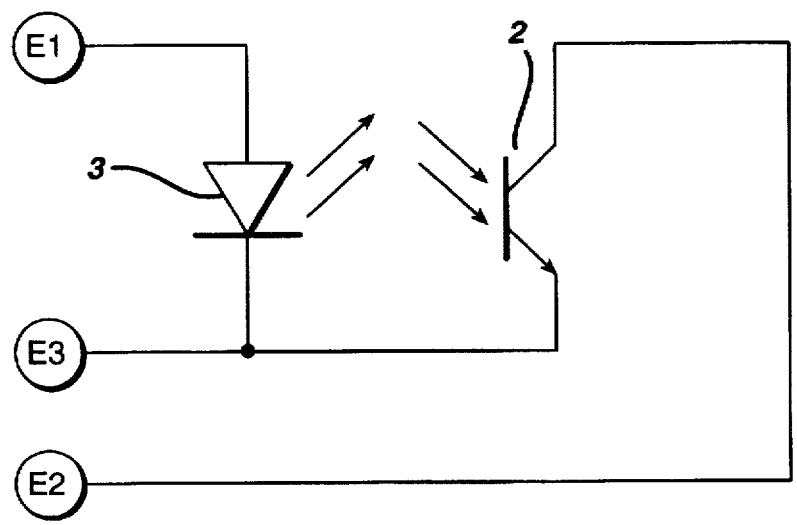

SURFACE SENSOR DEVICE

BACKGROUND OF THE INVENTION

This invention relates to a surface sensor device, particularly for use in sensing the proximity of a skin surface of a patient to which an optical instrument is being applied.

Many optical systems and instruments are used in medical practices and safety requirements dictate that the system or instrument should not be able to be activated in a manner that enables the optical beam to come into contact with the patient's or operator's eye. Light beams used in many optical systems and instruments applied for medical purposes are of a high intensity and can cause damage to an eye if the beam is accidentally directed into the eye.

Optical instruments include non-invasive clinical investigation devices which direct electromagnetic radiation from an optical outlet into the tissue of a patient through the patient's skin. Optical systems of this nature can include safety devices which disable the instrument when the light source is not in close proximity or contact with the patient's skin. Once a surface sensor is satisfied that the optical system is correctly positioned, the instrument becomes operable and the light source can be activated.

Known medical optical instruments have a number of surface sensors which are positioned around the optical outlet, which may be for example the end of an optical fibre. The sensors generally comprise a light emitting diode (LED) disposed adjacent a photodetector in the form of a phototransistor. As the skin surface is brought into proximity with the sensor device, the amount of light being reflected from the surface of the skin and detected by the phototransistor increases. The distance between the LED and the phototransistor in known surface sensors is 1–2 mm. Due to the distance between the LED and the phototransistor being small light absorption by the skin is also small, and so there is not a significant decrease in signal when the surface is brought into contact with the sensor. If the surface is not within a predetermined distance of the sensor device, the signal received by the phototransistor will not have reached a predetermined level and the instrument will be disabled.

A single sensor device positioned adjacent the optical outlet has the disadvantage of allowing a person to inadvertently pick up or hold the optical instrument covering the surface sensor but not the optical outlet and thereby enabling the operation of the optical instrument with the optical outlet directed away from the surface.

Two sensor devices, or preferably three devices, positioned around the optical outlet remove this possibility. However, such multiple sensor device systems have the disadvantage of being unwieldy and unnecessarily complicated due to the multiple wiring required.

It could have been envisaged that a compact sensor device might have been achieved by placing a light emitting diode on one side of the optical outlet and a photodetector on the opposite side of the optical outlet. This arrangement necessitates that the optical outlet is covered to enable the instrument to operate. In practice, however, when the skin surface is brought into contact with the sensor, the signal received by the photodetector is substantially less than the signal due to reflected light at some distance away from the surface. This is because the distance between the LED and the detector is relatively large (approximately 7 mm), and therefore a substantial proportion of the light is lost through absorption after multiple scattering beyond the skin surface.

SUMMARY OF THE INVENTION

It has been found that the signal received by the photodetector increases, as expected, as the distance between the sensor device and the skin surface decreases. However, a peak signal is reached when the skin surface is still a distance away from the sensor device. As the skin surface is brought still closer to the sensor device, the signal gradually decreases. This has the disadvantage that a predetermined level of signal is not a reliable indication of the proximity of the surface to the sensor device.

According to the present invention there is provided a surface sensor device comprising an electromagnetic radiation emitter and a radiation detector disposed on opposite sides of an instrument outlet, which instrument outlet is required to be placed in close proximity to a surface, and also comprising a member disposed in the path of the emitted radiation and the reflected radiation, wherein the member allows a portion of the emitted radiation to pass within it from the emitter to the detector while providing a path for a further portion of the radiation to pass through the member towards the surface for reflection from the surface and/or scattering and transmission from beyond the surface back towards the detector.

Preferably, the amount of radiation received by the radiation detector indicates the proximity of the instrument outlet to a surface.

Preferably, the member does not extend over the instrument outlet. The member may be in the form of a U or rectangular shaped plate surrounding an aperture at the instrument outlet.

The electromagnetic radiation may be infrared light.

Preferably, the radiation detector is a phototransistor and the radiation emitter is a light emitting diode.

Preferably, the member is an infrared transmission filter which has the advantage of removing unwanted background radiation from the radiation detector.

The instrument outlet may be in the form of a fibre optic light guide, terminating with a prism.

The radiation emitter and the radiation detector may be mounted on a printed circuit board to which the instrument outlet may be attached with the member being disposed parallel to the printed circuit board and sandwiching the radiation emitter and radiation detector.

BRIEF DESCRIPTION OF THE DRAWINGS

Embodiments of the present invention are now described, by way of example only, with reference to the accompanying drawings in which:

FIG. 6 is a plan of an assembly board of a surface sensor device in accordance with the present invention;

FIG. 7 is an underneath view of the assembly board of FIG. 6;

FIG. 8 is a circuit diagram of the components of the assembly board of FIG. 6.

DESCRIPTION OF THE PREFERRED EMBODIMENTS

Figure 1:
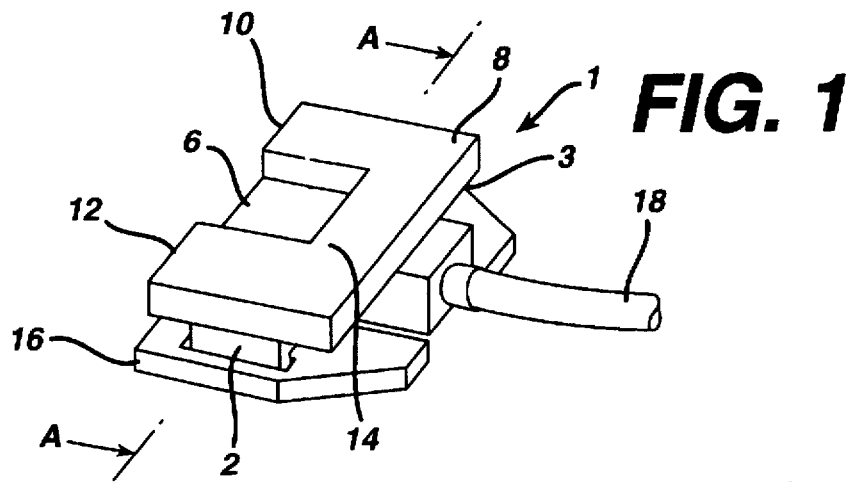
FIG. 1 is a perspective view of a first embodiment of a surface sensor device in accordance with the present invention.
Figure 3:
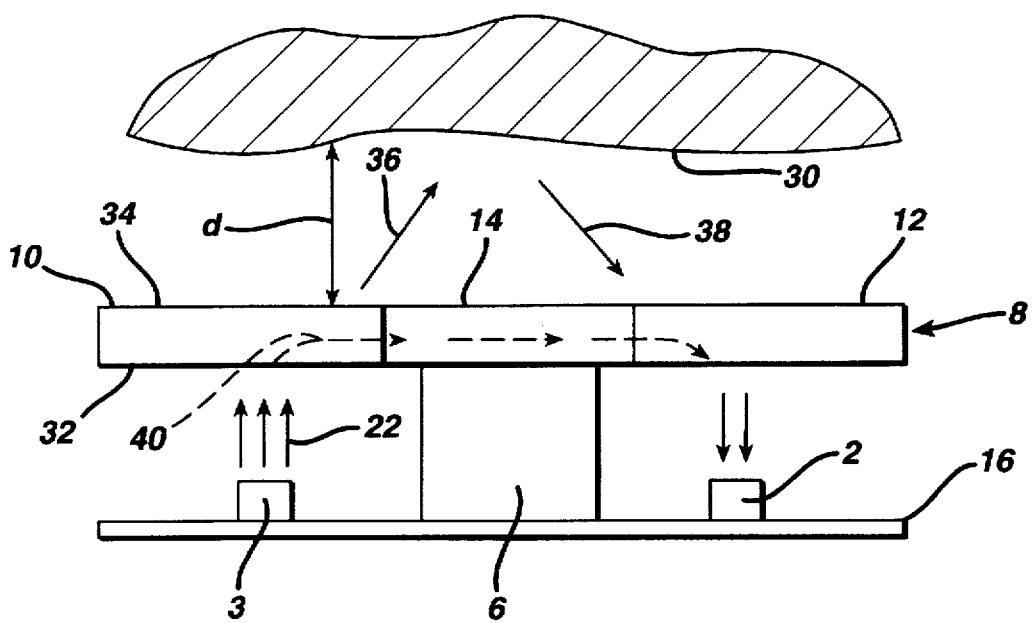
FIG. 3 is a cross-sectional view through the line A—A of FIG. 1.

Referring to the drawings, a first embodiment of a surface sensor device 1 for use with an optical instrument is shown in FIG. 1 and FIG. 3. The surface sensor device 1 has a radiation emitter in the form of a light emitting diode (LED) 3 and a radiation detector in the form of a phototransistor 2 both mounted on a printed circuit board 16. The LED 3 and the phototransistor 2 are disposed on either side of an optical outlet in the form of a prism 6 at the end of an optical fibre cable 18. A plate member 8 is disposed parallel to the printed circuit board 16 sandwiching the LED 3 and the phototransistor 2 between the member 8 and the printed circuit board 16.

In the first embodiment, the plate member 8 is of a U-shape with parallel leg members 10, 12 and a joining cross member 14. A first leg member 10 is disposed above the LED 3 in the path of the emitted radiation and a second leg member 12 is disposed above the phototransistor 2. The prism 6 is not covered by the plate member 8 as this is situated in the centre of the U-shape.

Figure 2:
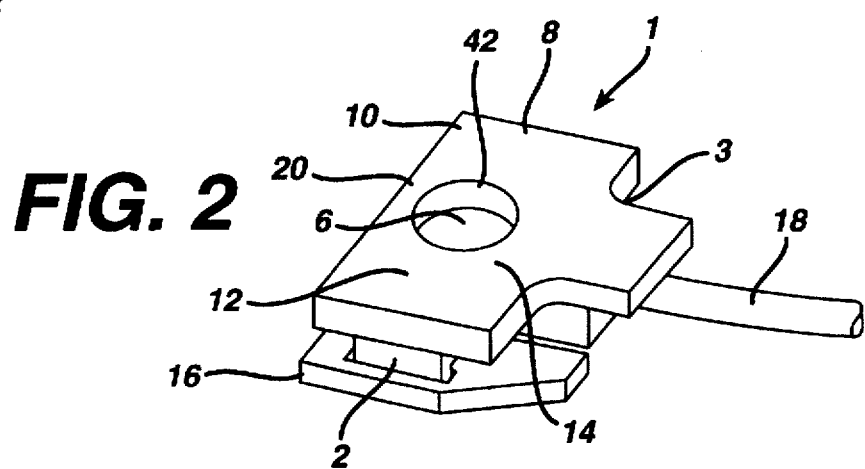
FIG. 2 is perspective view of a second embodiment of a surface sensor device in accordance with the present invention.

In a second embodiment of a surface sensor device 1 for use with an optical instrument as shown in FIG. 2, the plate member 8 is of a generally T-shaped form with a central portion removed to form a hole 42. The hole 42 may be circular, rectangular, square or of another configuration. The hole 42 is disposed at the prism 6 such that the prism 6 is aligned with the hole 42. The plate member 8 has two side portions 10, 12 and two end portions 14, 20. Again, the two side portions 10, 12 of the plate member 8 are disposed above the LED 3 and phototransistor 2 respectively.

The plate member 8 is T-shaped so as to provide a large surface area for adhering to the carrier of the prism 6.

Referring to FIG. 3, the optical outlet in the form of a prism 6 at the end of a fibre optic light guide is of greater height than the LED 3 and phototransistor 2. Therefore the plate member 8 is positioned across the top of the prism 6, providing a space between the LED 3 and phototransistor 2 and the lower surface of 32 of the plate member 8. The top surface 34 of the plate member 8 faces the skin surface 30 adjacent which the surface sensor device 1 is to be placed. A distance d between the upper surface 34 of the plate member 8 and the skin surface 30 is the distance being sensed by the surface sensor device 1. A predetermined distance d' is chosen as the maximum acceptable distance between the skin surface 30 and the upper surface 34 for the optical instrument to be operated safely and allowed to emit light.

Figure 9A:
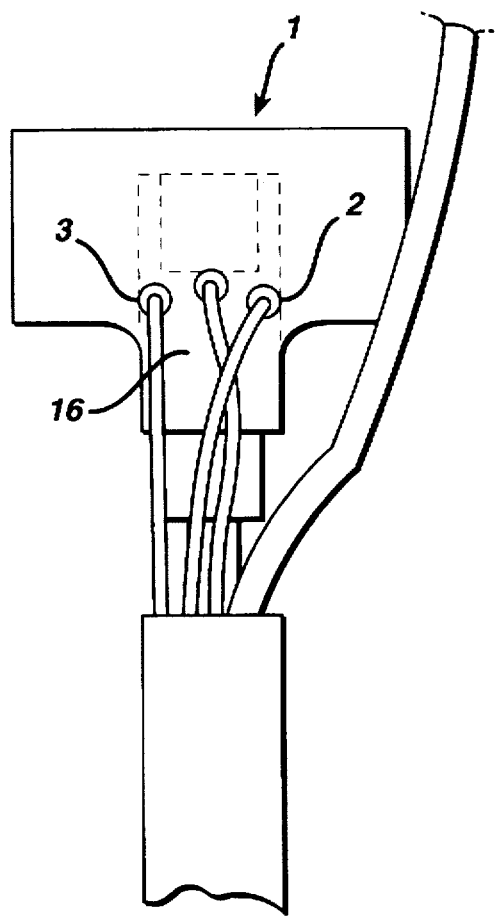
FIGS. 9a to 9c are back, side and cross-sectional views of a third embodiment of a surface sensor device in accordance with the present invention.
Figure 9B:
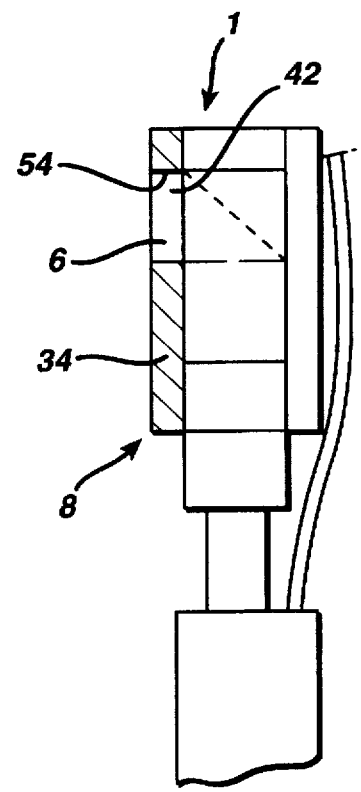
Figure 9C:
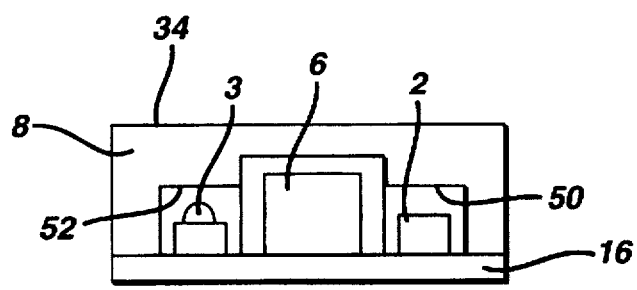

Referring to FIGS. 9a to 9c, a third embodiment of the surface sensor device 1 has a plate member 8 which is profiled to fit over the differing heights of the prism 6, the phototransistor 2 and the emitter 3 (see FIG. 9c). The profile of this embodiment facilitates assembly as the prism 6 is self-aligning in one direction. The depth of the profile is designed to make the phototransistor 2 and emitter 3 as close as possible to their adjacent surfaces 50, 52 of the plate member 8 to maximise optical coupling. The surfaces 50, 52 of the plate member 8 must be maintained scratch free during manufacture. The internal surface 54 of the hole 42 is polished. The material of the plate member 8 is Perspex black, burr free and polished where indicated.

The assembly board 16 which supports the components of the surface sensor device 1 is shown in FIGS. 6 and 7. The assembly board 16 forms a sandwich with the plate member 8 with the carrier of the prism 6 inbetween. The circuit of the phototransistor 2 and the emitter 3 is shown in FIG. 8.

In use, the surface sensor device 1 is placed in close proximity to or against a skin surface 30. The surface 34 exposed to the skin surface 30 is surrounded by a casing. Reflective foil can be wrapped around the outside of the device 1 to improve the response curve by helping to prevent light loss out of the sides of the plate assembly 8 into the surrounding casing. The upper surface 34 of the plate member 8 is closest to or adjacent the skin surface 30. The signal received from the phototransistor 2 indicates the distance d between the upper surface 34 of the plate member 8 and the skin surface 30. The signal from the phototransistor 2, in the form of a light intensity measure I, determines when the surface sensor device 1 is in close proximity to the skin surface 30 and it is safe to operate the optical instrument. If the surface sensor device 1 is tilted or moved away from the skin surface 30, the signal I produced by the phototransistor 2 will fall below a predetermined value I'. When the signal falls below the predetermined value I', the surface sensor device 1 renders the laser light source of the optical instrument inoperable.

The LED 3 emits infrared light of wavelength 830 nm. The plate member 8 is formed of an acrylic material which acts as an infrared transmission filter. A portion 36 of the light 22 emitted from the LED 3 passes through the plate member 8 and is reflected by the skin surface 30 or scattered or transmitted through the tissue beyond the surface 30. The reflected, scattered or transmitted light 38 passes back through the plate member 8 and is detected by the phototransistor 2. As the surface sensor 1 is almost or completely in contact with the surface 30, more of the light will enter the tissue beyond the surface 30 and be scattered before being received back in the light guide formed by the plate member 8.

The amount of light I being detected by the phototransistor 2 is attenuated as the skin surface 30 is moved away from the top surface 34 of the plate member 8. Light reaching the tissue will be scattered and reflected in all directions, and because of the increased distance from the plate member 8, very little is redirected back towards the phototransistor 2.

The LED 3 has a divergent beam. When the surface 30 is close to the sensor device 1, the divergence of the beam causes minimal light loss because much of the light from the LED 3 is scattered and reflected back towards the plate member 8 and guided towards the phototransistor 2 with little loss to free space. When the surface 30 moves away from the sensor device 1, the light illuminates a larger area of the surface 30 and therefore the intensity per unit area is substantially reduced. Any light reflected back towards the sensor device 1 will be of even lower intensity and will be reflected in all directions. The further the surface 30 is moved away, the more light is lost to free space and less is guided directly or indirectly by the plate member 8 towards the phototransistor 2.

The LED 3 is driven by a current pulse and the pulse signal received by the phototransistor 2 (in the form of the phototransistor) is a.c. coupled. This makes the system insensitive to ambient light which causes a d.c. offset at the phototransistor 2. The current pulse driving the LED 3 is positive going whereas the pulse signal received from the phototransistor 2 (due to the detection of the LED light pulse) is negative going. Therefore, if there is an electrical short circuit between the wires commenting the LED 3 and the phototransistor 2, the received short circuit signal will not be confused with a true signal.

The plate member 8 is also an infrared transmission filter (visible light blocking), and provides a secondary guard against background interference. The filter is useful for preventing saturation of the phototransistor 2 due to extremely high intensity light sources, for example hospital operating theatre lights. If the phototransistor 2 is saturated it will not detect a pulse signal and therefore the surface sensor 1 will prevent the operation of the laser light source. Saturation of the phototransistor 2 results in a non-functioning condition of the surface sensor 1, so the filter helps to prevent this non-functioning condition arising.

The plate member 8 acts as a light guide for a portion 40 of the light 22 emitted by the LED 3. A portion 40 of the light passing within the plate member 8 (shown in broken lines in FIG. 3) reaches the phototransistor 2 through this route. Light scattered and reflected from the surface 30 can also be guided back into the plate member 8 and towards the phototransistor 2. This takes place repeatedly along the length of the plate member 8 between the LED 3 and the phototransistor 2.

The existence of the plate member 8 helps to guide more of the light which is scattered and reflected by the surface 30 towards the phototransistor 2. Without the plate member 8 most of the light is quickly absorbed in the tissues beyond the surface 30 after multiple scattering.

Figure 4:
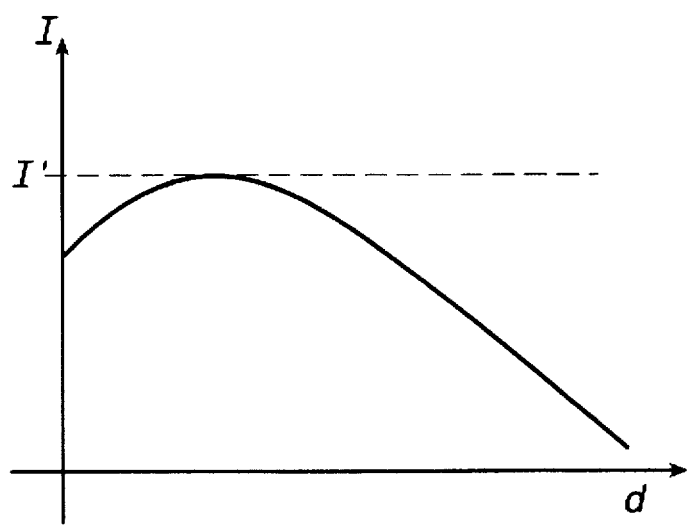
FIG. 4 is an illustrative graph of the signal received by a surface sensor device without a member.

FIG. 4 shows an illustrative graph of the relationship between the signal I received by the phototransistor 2 and the distance d from the skin surface 30 to an upper surface of a surface sensor device similar to that shown in FIG. 1 but without a plate member 8. In such a device the signal I decreases when the distance d is at its lowest values. Therefore, a predetermined value I' of the signal I can not be used as an indication of the distance d being below a certain value.

Figure 5:
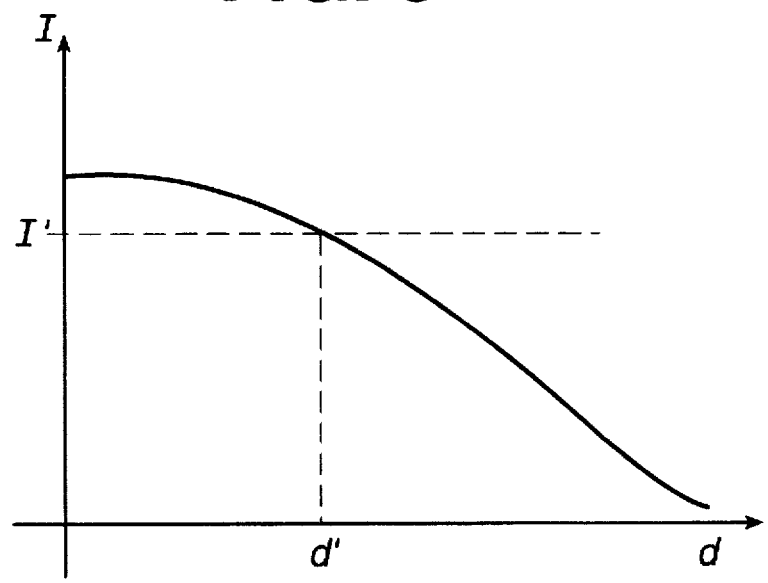
FIG. 5 is an illustrative graph of the signal received by a surface sensor device in accordance with the present invention.

FIG. 5 is an illustrative graph of the curve achieved (with the same relationship between the distance d and the signal I) when the plate member 8 is located between the skin surface 30 and the sensor device 1. The curve no longer decreases at low values of d and a threshold value I' can be used as an indication of when the distance d is below a predetermined distance d'.

It is envisaged that the surface sensor device 1 could be used with other types of instrument which require an indication of whether the instrument is adjacent or in close proximity to a surface. This invention is therefore not limited to the application of the surface sensor device 1 to a medical optical system or instrument.

The surface 30 can be a patient's skin and the optical instrument can be for non-invasive clinical investigation of a patient's tissue. Alternatively, the sensor device 1 can be used for other surface applications.

Modifications and improvements can be made to the above without departing from the scope of the present invention.

We claim:

1. A surface sensor device comprising an electromagnetic radiation emitter and a radiation detector disposed on opposite sides of an instrument outlet, which instrument outlet is required to be placed in close proximity to a surface, and also comprising a member disposed in the path of the emitted radiation and the reflected radiation, wherein the member allows a portion of the emitted radiation to pass within it from the emitter to the detector while providing a path for a further portion of the radiation to pass through the member towards the surface for reflection from the surface and scattering and transmission from beyond the surface back towards the detector.

2. A surface sensor device as claimed in claim 1, wherein the amount of radiation received by the radiation detector indicates the proximity of the instrument outlet to a surface.

3. A surface sensor device as claimed in claim 1, wherein the member does not extend over the instrument outlet.

4. A surface sensor device as claimed in claim 1, wherein the member is in the form of a U or rectangular shaped plate at least partially defining an aperture at the instrument outlet.

5. A surface sensor device as claimed in claim 1, wherein the electromagnetic radiation is infrared light.

6. A surface sensor device as claimed in claim 1, wherein the radiation detector is a phototransistor or photodiode and the radiation emitter is a light emitting diode.

7. A surface sensor device as claimed in claim 1, wherein the member is an infrared transmission filter which has the advantage of removing unwanted background radiation from the radiation detected.

8. A surface sensor device as claimed in claim 1, wherein the instrument outlet is in the form of a fibre optic light guide, terminating with a prism.

9. A surface sensor device as claimed in claim 1, wherein the radiation emitter and the radiation detector are mounted on a printed circuit board to which the instrument outlet is attached with the member being disposed parallel to the printed circuit board and sandwiching the radiation emitter and radiation detector.

* * * * *